United States Patent
Barkman et al.

(10) Patent No.: US 6,454,796 B1
(45) Date of Patent: Sep. 24, 2002

(54) VASCULAR GRAFT

(75) Inventors: Kimberley Barkman; Peter Ma, both of San Mateo; Richard S. Williams, Redwood City, all of CA (US)

(73) Assignee: Endovascular Technologies, Inc., Menlo Park, CA (US)

( * ) Notice: Subject to any disclaimer, the term of this patent is extended or adjusted under 35 U.S.C. 154(b) by 0 days.

(21) Appl. No.: 09/566,234

(22) Filed: May 5, 2000

(51) Int. Cl.$^7$ .................................................. A61F 2/06
(52) U.S. Cl. ...................................... 623/1.35; 623/1.36
(58) Field of Search ............................. 623/1.35, 1.36, 623/1.37, 1.49, 1.51, 1.52, 1.53, 1.54

(56) References Cited

U.S. PATENT DOCUMENTS

| | | |
|---|---|---|
| 3,530,904 A | 9/1970 | Ballard |
| 4,191,218 A | 3/1980 | Clark et al. |
| 4,530,113 A | 7/1985 | Matterson |
| 4,636,427 A | 1/1987 | Ohno et al. |
| 4,652,263 A | 3/1987 | Herweck et al. |
| 5,292,328 A | 3/1994 | Hain et al. |
| 5,413,598 A | 5/1995 | Moreland |
| 5,443,499 A * | 8/1995 | Schmitt ..................... 623/1.15 |
| 5,495,874 A | 3/1996 | Heiman |
| 5,508,094 A | 4/1996 | McCarthey et al. |
| 5,697,970 A | 12/1997 | Schmitt et al. |
| 5,824,047 A | 10/1998 | Moreland |
| 5,913,894 A | 6/1999 | Schmitt |
| 6,129,756 A * | 10/2000 | Kugler et al. ............... 623/1.27 |
| 6,136,022 A * | 10/2000 | Nunez et al. ................. 623/1.1 |
| 6,193,745 B1 * | 2/2001 | Fogarty et al. ............. 623/1.12 |
| 6,302,908 B1 * | 10/2001 | Parodi ....................... 623/1.31 |

* cited by examiner

Primary Examiner—Corrine McDermott
Assistant Examiner—Suzette J. Jackson
(74) Attorney, Agent, or Firm—Fulwider Patton Lee & Utecht, LLP (57) ABSTRACT

A bifurcated vascular graft having a tubular trunk with an inner diameter. Tubular limbs having respective inner diameters extend longitudinally from the trunk, and the diameter of at least one of the limbs is unequal to half the trunk diameter. In one embodiment, the graft is flared such that the combined diameters of the limbs exceed the diameter of the trunk. In another embodiment, the graft is tapered such that the diameter of the trunk exceeds the combined diameters of the limbs. In a third embodiment, the limb diameters are unequal to one another.

33 Claims, 6 Drawing Sheets

VASCULAR GRAFT

FIELD OF THE INVENTION

The present invention relates to the field of endovascular grafts for use in repairing aneurysms.

BACKGROUND OF THE INVENTION

Various fluid-conducting body lumens, such as veins, arteries, and ducts such as the bile duct, may deteriorate or suffer trauma so that repair is necessary. For example, various types of aneurysms or other deteriorative diseases may affect the ability of the lumen to conduct fluids and, in turn, may be life threatening. An aneurysm is a sac resulting from abnormal dilation of the artery wall. Unless treated, an aneurysm can rupture, leading to severe and often fatal hemorrhaging. Treating an aneurysm, for example an aortic aneurysm, generally involve implanting a prosthetic graft to bridge the affected section of the aorta. Surgical techniques known in the art involve major surgery in which a graft resembling the natural vessel, such as a donor graft or an artificial graft, is inserted into the diseased section of the natural vessel. Surgical implantation, however, causes considerable trauma, results in high mortality and morbidity and, even when completely successful, requires a lengthy recuperation period.

Medical improvements now also allow graft implantation to be done less invasively. In particular, endovascular surgery permits intraluminal repair using a catheter delivery system, without necessity for invasive surgery. The graft is packed into the delivery system and passed through the body lumen, for example through the femoral artery, to be implanted at the desired location. Generally speaking, intraluminal repair, where it is a viable alternative, can be performed more safely and with less trauma to the patient. Moreover, since intraluminal repair does not require major surgery, the recovery time from such a procedure is usually shorter.

Textile vascular grafts are widely used as prostheses to replace or repair damaged or diseased body lumens. Such grafts are generally formed by knitting, weaving or braiding suitable yarn. The endovascular prosthetic textile must be made very thin to permit introduction into the vessel via a catheter delivery system passed through the patient's vasculature. In addition, the graft must have high structural integrity to withstand pressures exerted on the graft by the fluid contained in the lumen and pressures exerted by subsequent balloon expansion on the catheter during implantation.

Treatment of an abdominal aortic aneurysm (AAA) commonly involves placement of a unibody bifurcated vascular graft having a tubular trunk section and a pair of tubular limb sections extending from the trunk section. When implanted endovascularly, the trunk section is secured within the abdominal aortic artery, while each of the limbs extends downwardly into one of the iliac arteries. Grafts available for this purpose fall into two general categories: unibody grafts and modular grafts. Unibody grafts are provided with the trunk and limb sections forming a single piece of textile with both limbs having sufficient length to reach the iliac arteries, respectively. Unibody grafts are implanted whole into the arterial system using a catheter delivery system, and manipulated to situate the trunk and limbs into their appropriate positions.

Modular grafts are provided in two or more separate sections. For example, one section may comprise the trunk, one of the limbs, and a stump limb that is not of sufficient length to extend into an iliac artery. The other section comprises the second limb to be mated with the stump limb to provide the length needed to extend into an iliac artery. The components are separately introduced into the patient's vasculature, typically with one section being introduced contralaterally and the other being introduced ipsilaterally. The sections are held together by friction or engagement after they have been separately introduced into the patient's vasculature.

Before s/he implants a vascular graft for AAA repair, the surgeon measures the respective diameters of the healthy portion of the abdominal aortic artery just below the renal arteries, and each of the iliac arteries. S/he then selects a graft of appropriate size for implantation. The unibody and modular grafts are typically provided in a variety of dimensions so as to accommodate a wide range of vessel sizes. The proportions of unibody grafts typically follow a standard formula in which the trunk has a first inner diameter and in which the limbs are equal in inner diameter to one another. The inner diameter of each limb is one-half the inner diameter of the trunk. In other words, a 26 mm graft would have a trunk diameter of 26 mm, and two limbs each 13 mm in diameter. This standard proportion for unibody grafts is due to manufacturing considerations. The grafts are generally formed by knitting, weaving or braiding suitable yarn.

Because modular grafts are provided in multiple pieces, a surgeon may elect to implant limbs of unequal diameters if the patient's vessel diameters warrant doing so. In this regard, modular grafts are beneficial in that they provide the surgeon with a greater number of size options for each patient. However, modular grafts suffer from potential drawbacks in that the pieces of the graft may leak at their junction or become disconnected after they have been introduced into the patient's vasculature. Disconnects can lead to undesirable leaks or ruptures in the graft or vessel.

It is highly desirable to increase the population of patients eligible for intraluminal AAA repair in order to minimize the number of patients who must undergo the more complicated open surgical procedure. It is thus desirable to provide a unibody vascular graft which is not limited by the standard formula for graft dimensions and that thus provides the surgeon with numerous size options for each patient, and that also does not have the risk of disconnecting or leaking,.

To provide consistency with the common usage of terms used in the medical surgical arts in the United States, the terms "inferior and superior"are used with a certain regularity within the present specification. Superior refers to a location situated above and is used herein in the description of the graft and attachment system. Inferior refers to the point situated below and again is used herein with the graft and attachment system. Thus, for applications in the abdominal aorta which use a femoral approach, the superior end of the graft resides within the aorta. Likewise, the inferior ends of the graft reside within the iliac arteries.

The term "ipsilateral" typically refers to a vessel or part of a device which resides on the same side in which a device enters a lumen. For example, the ipsilateral tubular leg of a graft would be the tubular leg which resides in the iliac artery in which the delivery catheter enters the aorta. Similarly, the term "contralateral" refers to a vessel or device residing on the opposite side of which the catheter enters the aorta. For example, the contralateral attachment system resides in the contralateral iliac artery which is on the opposite side of the aorta from which the delivery catheter enters the aorta.

SUMMARY OF THE INVENTION

The present invention is a unibody or modular bifurcated vascular graft having a tubular trunk with an inner diameter.

Tubular limbs having respective inner diameters extend longitudinally from the trunk, and the diameter of at least one of the limbs is unequal to half the trunk diameter. In one embodiment, the graft is flared such that the combined diameters of the limbs exceed the diameter of the trunk. In another embodiment, the graft is tapered such that the diameter of the trunk exceeds the combined diameters of the limbs. In a third embodiment, the limb diameters are unequal to one another. Additional embodiments utilize tapers and/or flares having various positions relative to the superior and inferior regions of the graft.

DETAILED DESCRIPTION

The present invention is directed to vascular graft having a tubular trunk and at least two tubular limbs extending from the trunk. The trunk and limbs are proportioned such that the limbs are not simply half the diameter of the trunk, so as to offer the surgeon a greater number of sizing options for patients requiring graft implantation. In an optimal situation, the surgeon would have access to a selection of grafts having varying combinations of trunk and limb diameters. This allows the surgeon to choose a graft that best fits the vasculature of the patient in which the implantation is being performed.

For simplicity, exemplary embodiments will be described that utilize woven textiles as the graft material, although it should be appreciated that grafts according to the present invention may be formed by weaving, knitting or non-woven techniques such as electrostatic spin bonding or sewing. Typically, a woven graft textile includes a first set of yarns oriented in the end direction and a second set of yarns oriented in the pick direction, which are woven together to form the prosthetic textile. As it is known in the art of textile weaving, "end" yarns are oriented parallel to each other in an axial direction, and are raised and lowered during the weaving process to provide a space for the "pick" yarns. The pick yarns, being oriented perpendicularly to the end yarns in a lateral direction, are then carried in the pick direction in the provided space across the width of the ends by different types of mechanisms, for example by a shuttle, rapier, projectile, air jet or water jet, thereby weaving the prosthetic textile.

We define yarn as a strand of textile fiber made up of one or more filaments. Thus, the yarns used in the exemplary embodiments may be constructed either from a single filament (monofilament) or from multiple filaments (multifilament). The filaments that comprise the yarn may be associated with each other in any manner, for example by being twisted around each other or interlaced. The yarns may be textured or flat, and may be of any opacity, for example bright, semi-dull, and full-dull. The yarns used to weave the prosthetic textile of the invention may be biologically compatible, for example natural materials such as ilk, and synthetic materials such as polymers, for example polyethylene terephthalate (PET) or ultra high molecular weight polyethylene (UHMWPE). Biologically incompatible yarn may also be used, such as cotton and the resulting prosthetic may be coated or otherwise treated with a suitable biocompatible material to permit entrance into the body. Preferably, the yarn used is made from PET.

In constructing a graft from prosthetic textile, the yarns in the end and pick directions may be woven together in any weave configuration, for example plain, twill, satin, velour, double velour, and basket weave. The woven prosthetic material may be directly manufactured into a seamless tubular configuration having a trunk wall defining at least one lumen extending therethrough, and branched with two or more limbs extending from the graph body (e.g. it can be bifurcated or trifurcated). Such a seamless configuration may be manufactured using weaving methods known in the art, for example by employing a shuttle loom. The end yarns in the tubular configuration are oriented along the longitudinal axis of the tube or branch, while the pick yarns are oriented radially around the tube or branch.

Alternatively, the woven prosthetic material is manufactured in sheet form and later formed into a cylindrical trunk with branched limbs. Again, the end yarns in the tubular configuration are oriented along the longitudinal axis of the tube, while the pick yarns are oriented perpendicular to the longitudinal axis.

Figure 1A:
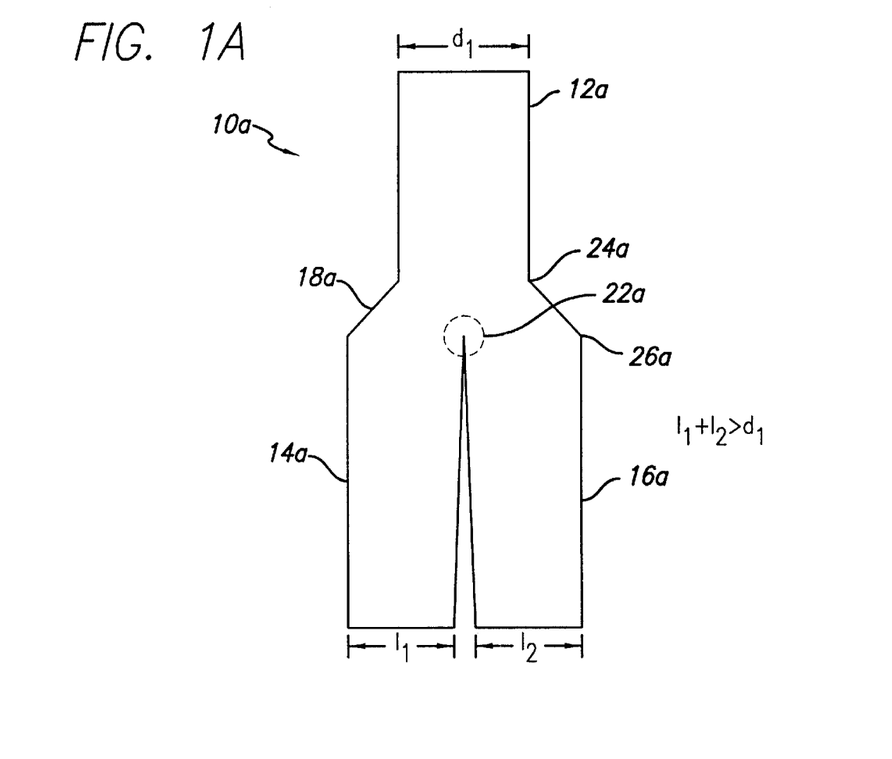
FIG. 1A is a front elevation view of a flared vascular graft utilizing principles of the present invention.
Figure 1B:
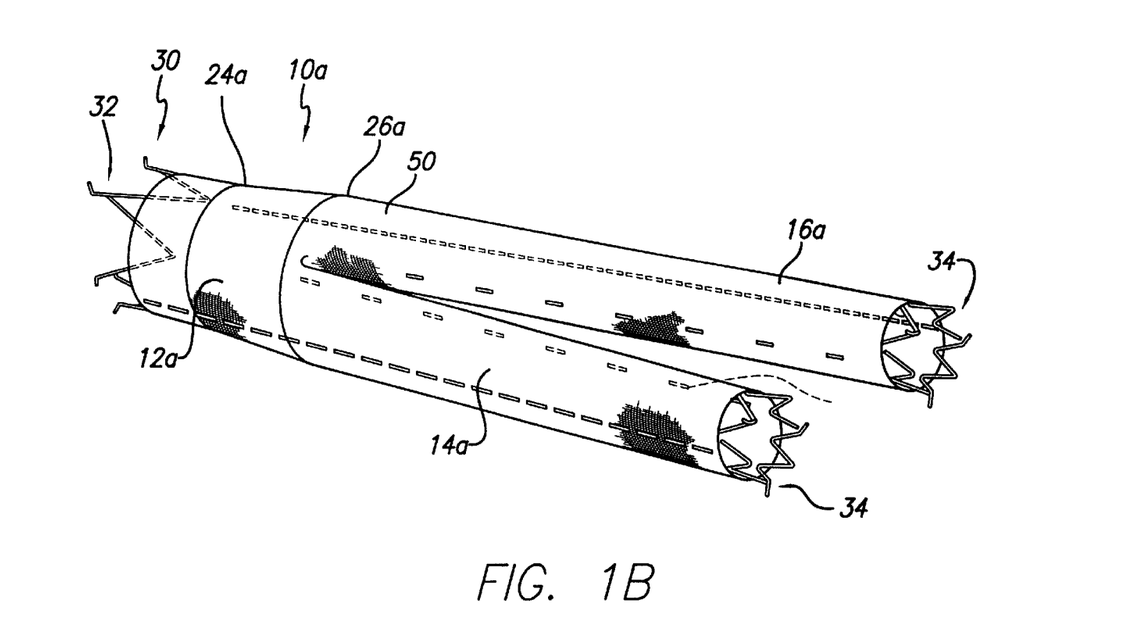
FIG. 1B is a perspective view of the flared vascular graft of FIG. 1A.

A first embodiment of a vascular graft $10a$ is shown in FIGS. 1A and 1B. The graft $10a$ includes a tubular trunk $12a$ having an inner diameter $d_1$. Tubular limbs $14a$ and $16a$ having inner diameters $I_1$ and $I_2$, respectively, extend longitudinally from the trunk $16a$. For clarity, the two tubular legs are referred to herein as the ipsilateral tubular limb $14a$ and the contralateral tubular limb $16a$. Graft $10a$ includes a flared section $18a$ at which the flat width of the graft gradually increases. Because the graft is flared, the sum of diameters $I_1$ and $I_2$ is greater than the diameter $d_1$ of the trunk $12a$. The limb diameters may be equal to one another or unequal to one another, as illustrated in the examples below. Although each of the illustrated embodiments utilizes two limbs, it should be appreciated that embodiments utilizing more than two limbs may also be configured utilizing principles of the present invention Flare 18a in the graft 10a may be formed using a fan reed at the loom to gradually spread the end yarns further apart from one another. It is important, however, to maintain a suitable fabric density so as to give the textile the necessarily fluid impermeability (typically a desired range of fluid permeability for a graft of this type is approximately 50–450 ml/cm$^2$ min) and burst strength. Thus, fanning the end yarns must be accompanied by a corresponding insertion of additional pick or end yarns into the fabric so as to maintain suitable fabric density.

The graft 10a is typically formed of two layers of the desired textile. At the region at which the bifurcation occurs, called the septum 22a, the layers may be sewn or woven together so as to prevent separation of the layers.

In this and in each of the described embodiments, the limbs 14a, 16a may be equal or unequal in length relative to one another.

Table 1 gives sample specifications for an embodiment such as the FIG. 1A–1B embodiment, in which the trunk inner diameter $d_1$ is 20 mm, and the limb inner diameters $I_1$ and $I_2$ are equal to one another at 12 mm each. The sample graft is a plain weave tubular graft in which the end yarns (also called warp yarns) are polyester and in which the pick yarns (also called weft or filling yarns) are likewise polyester. The graft is formed of two layers of the woven textile. As can be seen, the number of picks/inch and ends/inch increase from trunk to limb so as to maintain fabric density despite the flare in the graft textile.

TABLE 1

| TRUNK 20 mm/LIMBS 12 mm, 12 mm | |
| --- | --- |
| PICKS/INCH: Trunk | 80–110 per face |
| ENDS/INCH: Trunk | 115–150 per face |
| PICKS/INCH: Limb | 90–105 per face |
| ENDS/INCH: Limb | 100–125 per face |
| Total Graft Ends | 333–369 |

Table 2 gives sample dimensions for a second graft such as graft 10a of FIGS. 1A–1B, but in which the trunk inner diameter $d_1$ is 26 mm, and the limb inner diameters $I_1$ and $I_2$ are unequal to one another at 14 mm and 16 mm, respectively. The sample graft is a plain weave tubular graft in which the warp and weft yarns are polyester. The graft is formed of two layers of the woven textile.

TABLE 2

| TRUNK 26 mm/LIMBS 14 mm, 16 mm | |
| --- | --- |
| PICKS/INCH: Trunk | 80–100 per face |
| ENDS/INCH: Trunk | 115–150 per face |
| PICKS/INCH: Limb | 90–110 per face |
| ENDS/INCH: Limb | 100–130 per face |
| Total Graft Ends | 417–564 |

For the repair of an aortic aneurysm, the length of the graft is selected so as to span approximately one centimeter superior and one centimeter inferior of the aneurysm. The graft should be about two centimeters longer than the aneurysm being treated. Limbs 14a, 16a may be equal or unequal to one another in length.

Graft 10a includes attachment systems 32, 34 with wall engaging members secured to the superior end of the tubular trunk 12a and the inferior ends of the tubular limbs 14a, 16b. Attachment systems 32, 34 include members which seat within normal tissue of the vessel on both sides of the aneurysm.

Figures 1C, 1D:
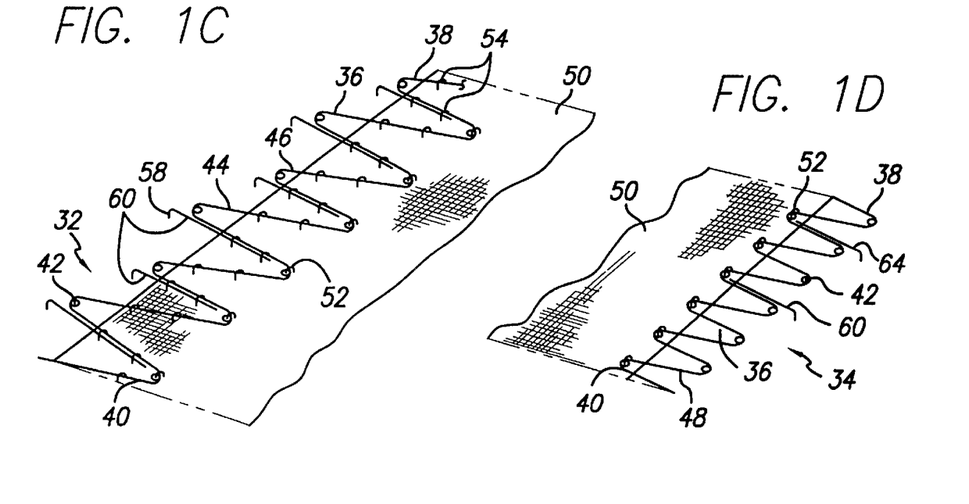
FIG. 1C is a top plan view showing a superior attachment system as sewn into the main tubular trunk of the graft of FIG. 1A.
FIG. 1D is a top plan view showing an inferior attachments as sewn into a tubular limb of the graft of FIG. 1A.

Referring to FIG. 1C, a self-expanding superior attachment system 32 is secured adjacent the superior end 30 of the tubular trunk 12a. As shown in FIG. 1D, a first self-expanding inferior attachment system 34 is secured adjacent the inferior end of the ipsilateral tubular limb 16a. Similarly, a second self-expanding inferior attachment system 34 is secured adjacent the inferior end of the contralateral tubular limb 14a. Each attachment system serves to yieldably urge the graft 10a from a first compressed or collapsed position to a second expanded position and provides a fluid tight seal between the graft and corporeal lumen wall.

Each attachment system is formed of a plurality of vees 36 with the outer apices 38 and inner apices 40 of the vees being formed with helical torsion springs 42. The attachment system may be comprised of apices numbering from four to twenty-four. The springs yieldably urge the limbs of each of the vees outwardly at a direction approximately at right angles to the plane in which each of the vees lie. The superior attachment system 32 has both long limbs 44 and short limbs 46 which stagger the apices along the superior end of the graft 10a. The limbs 48 of the inferior attachment system 34, however, are of equal length.

Figure 1E:
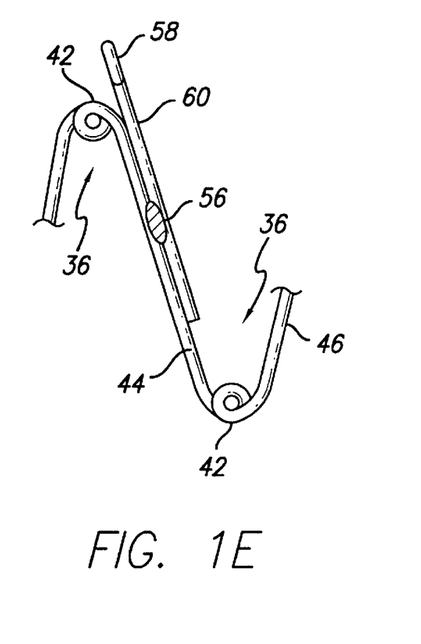
FIG. 1E is an enlarged side plan view showing a superior attachment system.

As shown in more detail in FIG. 1E, the superior attachment system 32 is comprised of a single piece of wire which is formed to provide the vees 36 and also to define the helical torsion springs 42 between the limbs 44 and 46. The two ends of the single piece of wire can be welded together in one of the limbs to provide a continuous spring-like attachment system. In the construction shown in FIGS. 1A and 1C, it can be seen that the attachment systems have twelve apices lying in three longitudinally spaced-apart parallel planes which are spaced with respect to the longitudinal axis of the main tubular trunk 12a. The outer apices 38 residing external of the graft are staggered; whereas, the inner apices 40 residing within the graft lie in the same plane. Similarly, the apices will lie in four planes if the inner apices are also staggered.

The superior and inferior attachment systems 32 and 34 are secured to the wall 50 of the graft 10a by suitable means such as a polyester suture material. As shown in FIGS. 1C and 1D, sutures or knots 52 are used for sewing the inner apices 40 onto toe wall of the main tubular trunk 12a and each tubular limb 16a and 14a. Additional sutures 54 are preferably formed on each of the superior limbs 44 and 46 to firmly secure each limb to the graft. The limbs may be secured so that the apices lying in each plane are staggered to provide for the minimum profile when the attachment system is placed in its collapsed condition.

As shown in FIG. 1E, wall engaging members 60 are preferably secured to the limbs 44 and 46 of the attachment systems 32 and 34 in the vicinity of the outer apices 38 by suitable means such as a weld 56. The wall engaging members have a diameter ranging from 0.007 to 0.018 inches (0.254–0.457 mm) and a length from 0.5 to 5.0 millimeters. The wall engaging members are preferably sharpened to provide conical tips 58, and should have a length which is sufficient for the tip to penetrate into and perhaps through the corporeal lumen wall. The wall engaging members of the inferior attachment system 34 are configured in a similar manner.

The superior attachment system 32, inferior attachment system 34 and the wall engaging members 60 secured thereto are formed of a corrosion resistant material which has good spring and fatigue characteristics. One such material found to be particularly satisfactory is "ELGILOY" which is a cobalt-chromium-nickel alloy manufactured and sold by Elgiloy of Elgin, Ill. The wire can have a diameter ranging from 0.008 to 0.016 inches (0.203–0.406 mm), with a smaller diameter wire being utilized for the smaller diameter grafts. For example, 0.012 to 0.016 inch (0.305–0.406 mm) diameter wire for the frame and wall engaging members may be used in the larger grafts of eighteen to twenty-eight millimeters diameter, and 0.008 to 0.012 inch (0.203–0.305 mm) diameter wire may be used in the smaller grafts being eight to sixteen millimeters in diameter.

It has been found that the spring force created by the helical torsion springs 42 at the apices 38 and 40 is largely determined by the diameter of the wire. The greater the diameter of the wire, the greater the spring force applied to the limbs 44 and 46 of the vees. Also, the longer the distances are between the apices, the smaller the spring force that is applied to the limbs. It therefore has been desirable to provide a spacing of approximately fifteen millimeters between the outer extremities of the limbs 44 of the superior attachment system 32. Similarly, a spacing of approximately ten millimeters between the outer extremities of the limbs 48 of the inferior attachment system 34 is preferable, although smaller or larger distances may be utilized.

Figure 1F:
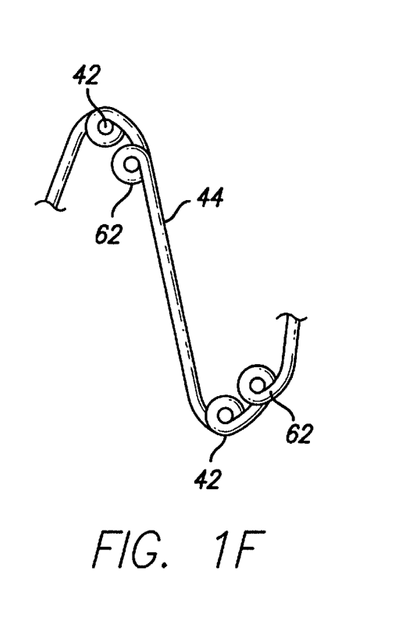
FIG. 1F is an enlarged side plan view showing an attachment system having a supplemental helix torsion spring at the apices.

FIG. 1F shows a low stress configuration of an superior attachment system 32 or inferior attachment system 34. An additional helical torsion apex 62 is added along the limbs 44, 46 or 48 of the attachment system. The additional apices are located adjacent the apices at the vees 36 formed by the limbs. Such a configuration improves the fatigue characteristics of the attachment system. In addition, the weld 56 for the wall engaging members 60 may be moved down the attachment system limb 44 or 46 to improve fatigue life. Alternatively, a non-round or non-circular wire, for example, a rectangular, conical or rounded ribbon wire, may be used to reduce the amount of stress in the attachment system and still maintain the spring force of the attachment system.

To facilitate securing the graft 10a in the corporeal lumen, the conical tips 58 of the wall engaging members 60 on the superior attachment system 32 may be angled with respect to longitudinal axis of the main tubular trunk 12a. The wall engaging members face outwardly from the main tubular trunk to facilitate holding the graft in place.

Preferably, the conical tips of the wall engaging members on the superior attachment system are inclined from the longitudinal axis and toward the inferior end of the graft by 10a. degree. to 90.degree. and preferably about 85.degree. Likewise, the conical tips 64 of the wall engaging members on the inferior attachment system 34 may be inclined towards the superior end of the graft by 30.degree. to 90.degree. and preferably 85.degrees.

By angling the conical tips of the wall engaging members so that they resist the force of the blood flow, the implanted wall engaging members oppose migration of the graft.

The helical torsion springs 42 placed at the apices 38 and 40 20 serve to facilitate compression of the graft 10a to place the superior and inferior attachment system 32 and 34 within the capsule assemblies 90, 130 and 200, as hereinafter described. The compression of the graft is accomplished by deformation of the helical torsion springs to just outside their elastic limit, thereby having a small component within the plastic range. Placing the apices in different planes and staggering or offsetting the wall engaging members 60 significantly reduces the minimum compressed size of the graft. Having the conical tips 58 and 64 in different planes also helps to prevent the wall engaging members from becoming entangled with each other. The natural spring forces of the helical torsion springs serves to expand the graft to its expanded position as soon as the attachment system is free of the capsules.

Implantation of a bifurcated vascular graft having attachment systems of the type just described is set forth in detail in U.S. Pat. No. 5,769,885, the disclosure of which is incorporated herein by reference. Briefly stated, a catheter system, which may be of the type described in U.S. Pat. No. 5,769,885, is used to position the trunk in the aorta and the limbs 14a, 16a in the contralateral and ipsilateral iliac arteries, respectively. A balloon is inflated within each of the trunk and limbs to firmly seat the wall engaging members 60 into the surrounding vessel wall.

Figure 2A:
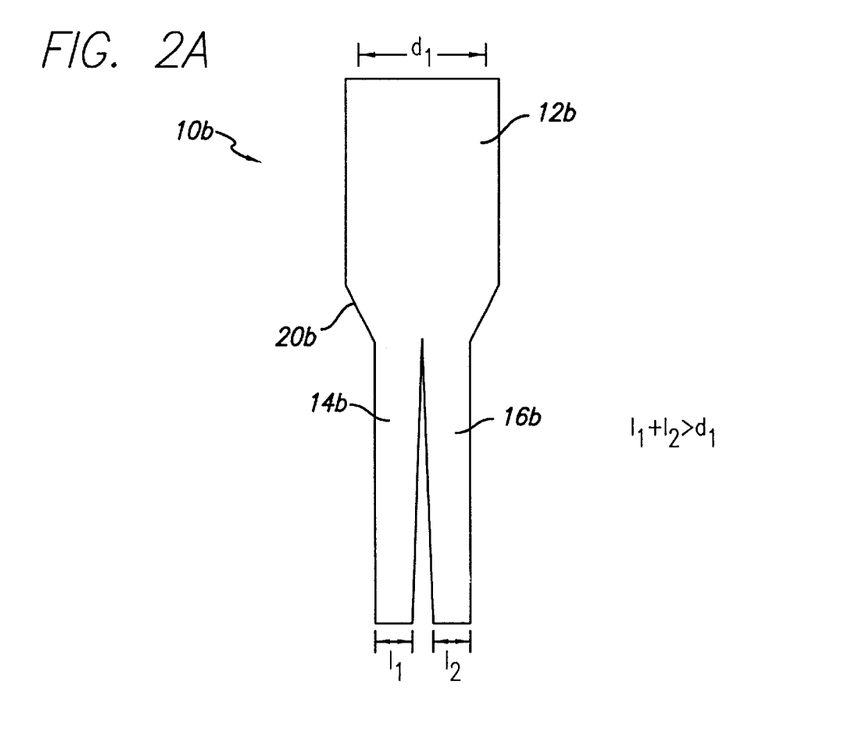
FIG. 2A is a front elevation view of a tapered vascular graft utilizing principles of the present invention.
Figure 2B:
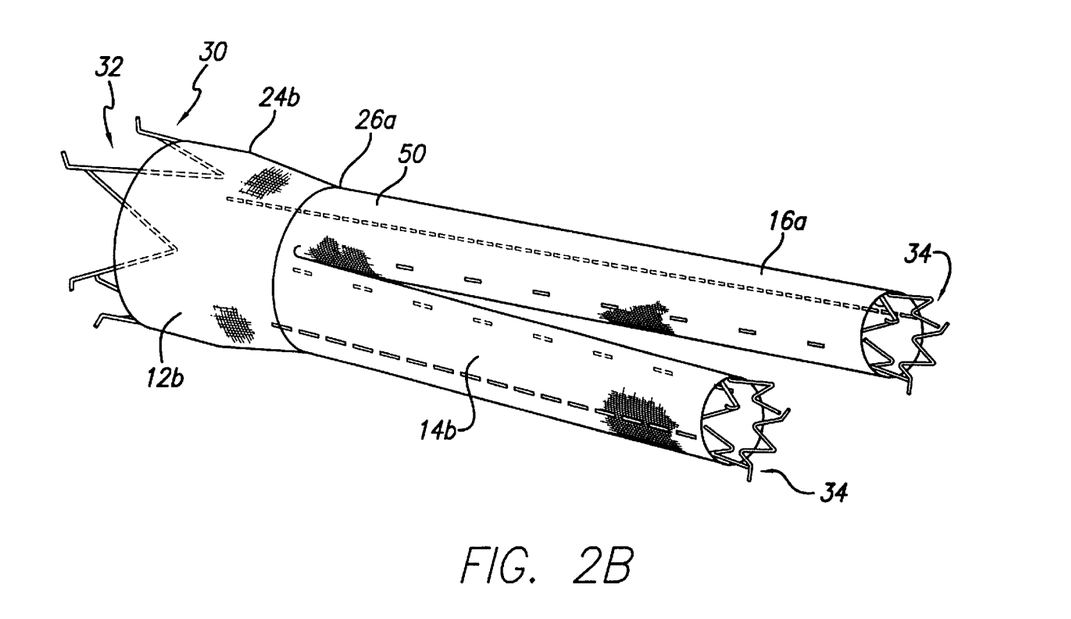
FIG. 2B is a perspective view of the tapered vascular graft of FIG. 2A.

FIGS. 2A–2B show an embodiment of a graft 10b in which the graft is tapered from the trunk 12b to the limbs 14b, 16b. For simplicity, the attachment system is only shown in the perspective view of FIG. 2B. The attachment system may be of the type described with reference to FIGS. 1A–1F and thus will not be repeated here. A tapered section 20b extends between the trunk and limbs. The tapered section can be above, below or at the graft bifurcation.

The taper in the graft 10b may be formed using a fan reed at the loom to gradually bring the end yarns closer together. This must be accompanied by a corresponding reduction in density of the end or pick yarns to prevent bunching of the yarns at the limbs. To achieve reduction of ends, it may be necessary to remove some ends from weaving.

Figure 3:
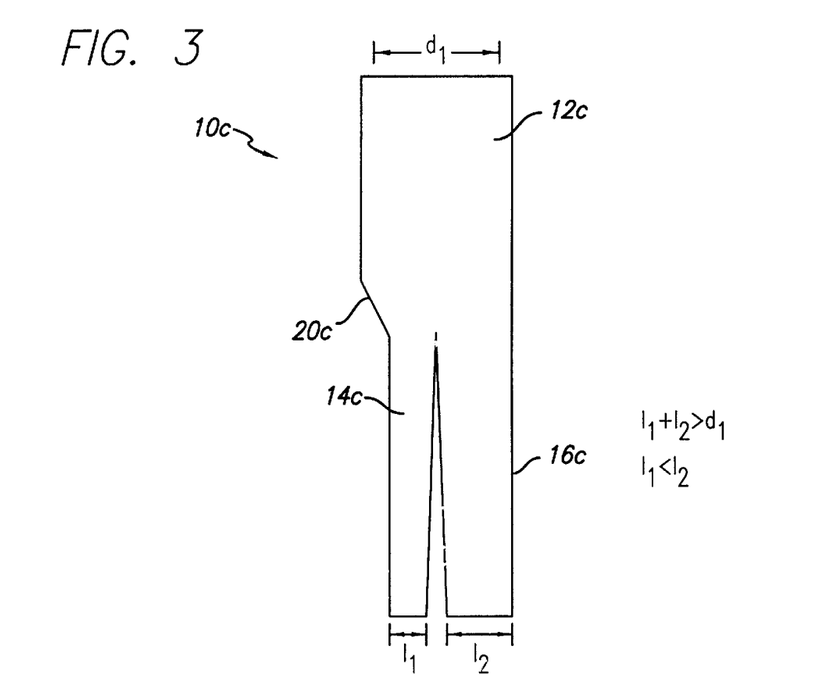
FIG. 3 is a front elevation view of a second embodiment of a tapered vascular graft utilizing principles of the present invention.

As with the FIG. 1A–1B embodiment, limbs 14b, 16b may have equal inner diameters (e.g. d=26 mm; $I_1=I_2=12$ mm), or their inner diameters may be different (e.g. d=26 mm; $I_1=10$ mm; $I_2=12$mm). FIG. 3 shows an alternative embodiment of a graft 10c in which the limbs are unequal in diameter. The FIG. 3 embodiment differs from the FIG. 2A–2B embodiment, however, in that only one side of the graft 10c has a tapered section 20c extending between the trunk 12c and the limb 14c which has the smaller diameter. It should be appreciated that the FIG. 1A embodiment may be similarly modified to include a flared section leading to only one of the limbs 14a or 16a, rather than the flared section 18a which meets both limbs.

Figure 4:
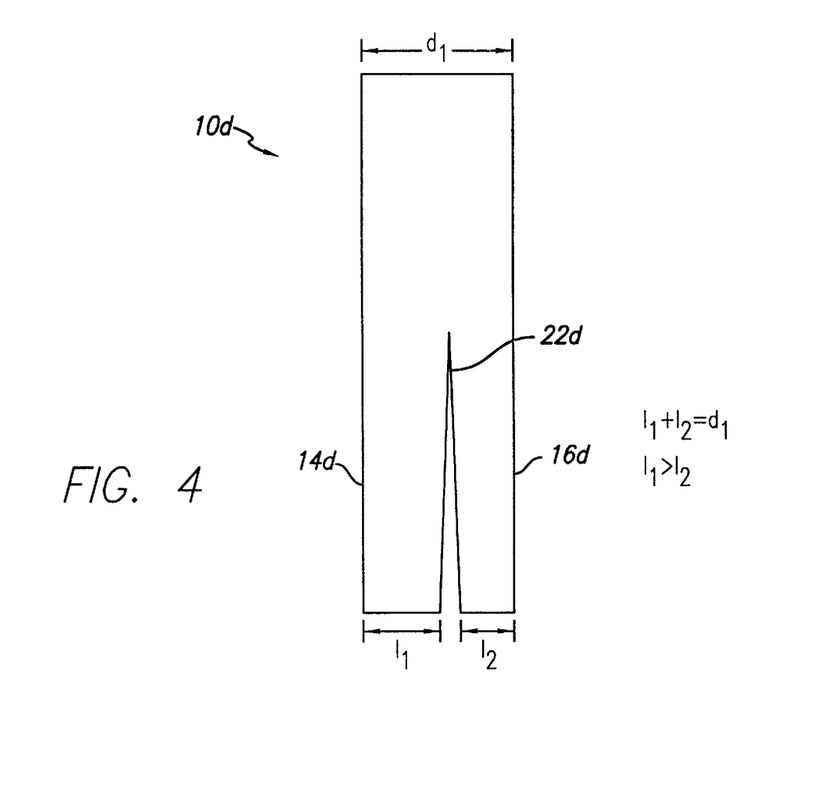
FIG. 4 is a front elevation view of an embodiment of a vascular graft utilizing principles of the present invention.

A fourth embodiment of a vascular graft 10d is shown in FIG. 4. The fourth embodiment may utilize an attachment system such as that of the type described with respect to FIGS. 1A–1F.

The FIG. 4 embodiment differs from the others in that it is neither tapered nor flared. The asymmetrical limb configuration is accomplished by offsetting the bifurcation 22d from the longitudinal center axis of the graft. The diameters of the iliac limbs 14d, 16d are unequal to one another, but the sum of the limb diameters approximately equals the trunk diameter (i.e. within approximately +/−1.5 mm). Dimensions for an example of a graft of this type, which has a trunk diameter of 22 mm and limb diameters of 12 mm and 10 mm, respectively, are provided in Table 3.

TABLE 3

TRUNK 22 mm; LIMBS 12 mm, 10 mm

| | |
|---|---|
| PICKS/INCH: Trunk | 85–100 per face |
| ENDS/INCH: Trunk | 115–135 per face |
| PICKS/INCH: Limb | 85–100 per face |
| ENDS/INCH: Limb | 115–135 per face |
| Total Graft Ends | 345 |

It is highly desirable to provide a surgeon with a selection of grafts having varying combinations of trunk and limb diameters, typically with trunk sizes ranging between 20–30 mm, and with limb sizes ranging between 10–18 mm. This allows the surgeon to select a graft having iliac limbs and an aortic trunk that best match the sizes of the patient's iliac and aortic arteries.

Figure 5A:
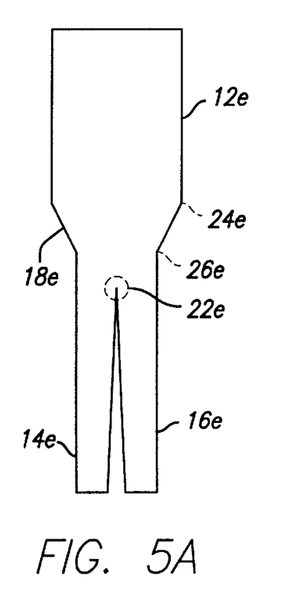
FIGS. 5A–5C are front elevation views of embodiments of tapered vascular grafts utilizing principles of the present invention, and showing the taper located superior to, at, and inferiorly of the bifurcation, respectively.
Figure 5B:
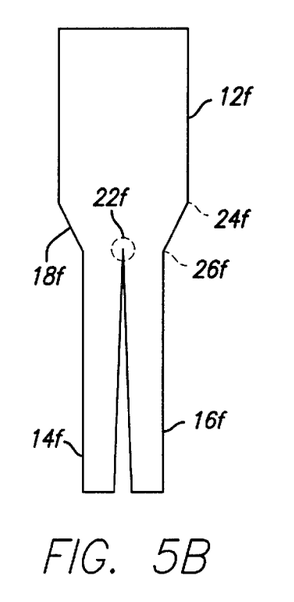
Figure 5C:
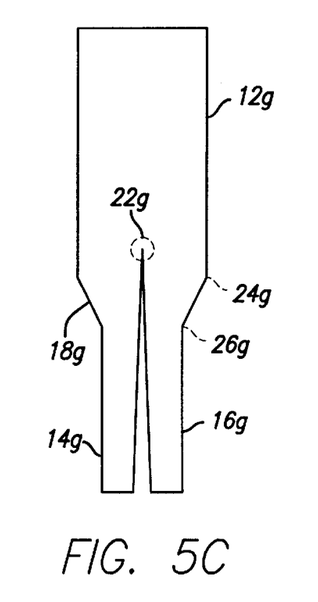

It should be appreciated that the longitudinal position of the taper or flare may vary relative to the longitudinal position of the septum. FIGS. 5A, 5B and 5C show three embodiments of tapered vascular grafts, each of which utilizes a different longitudinal position for the taper.

FIG. 5A illustrates a taper 18e positioned superiorly of the bifurcation point (or septum) 22e. In other words, both the superior end 24e and the inferior end 26e of the taper are positioned superiorly of the bifurcation point 22e.

FIG. 5B illustrates a taper positioned "at" the bifurcation, in that the superior end 24f of taper 18f is located superiorly of bifurcation point 22f, and inferior end 26f of taper 18f is located inferiorly of bifurcation point 22f. Taper 18g of the embodiment of FIG. 5C is positioned inferiorly of bifurcation point 22g, since both its superior end 24g and its inferior end 26g are positioned inferiorly of bifurcation point 22g.

Figure 6A:
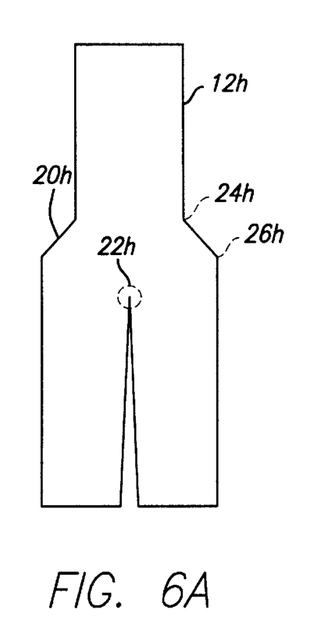
FIGS. 6A–6C are front elevation views of flared vascular grafts utilizing principles of the present invention, and showing the flare located superior to, at, and inferiorly of the bifurcation, respectively.
Figure 6B:
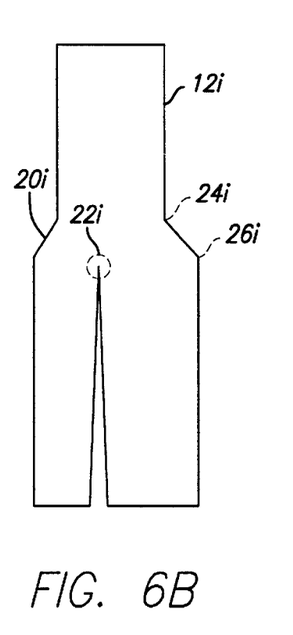
Figure 6C:
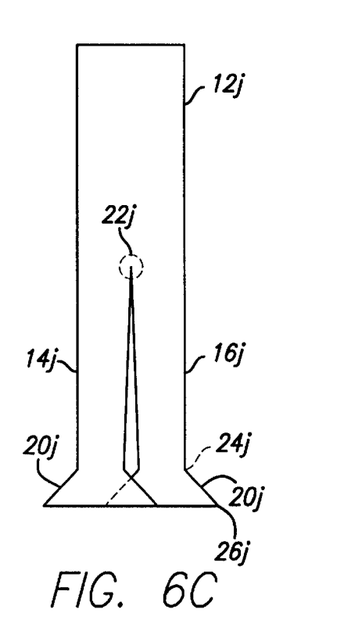

FIGS. 6A–6C show three flared vascular grafts, each of which utilizes a different longitudinal position for the flare. In FIG. 6A, the flare 20h is located superiorly of the bifurcation point 22h, since it is superiorly located relative to the superior and inferior ends 24h, 26h of the flare 20h. In FIG. 6B, the flare is "at" the bifurcation, since bifurcation point 22i lies longitudinally between superior end 24i and inferior end 26i of flare 20i.

Figure 10:
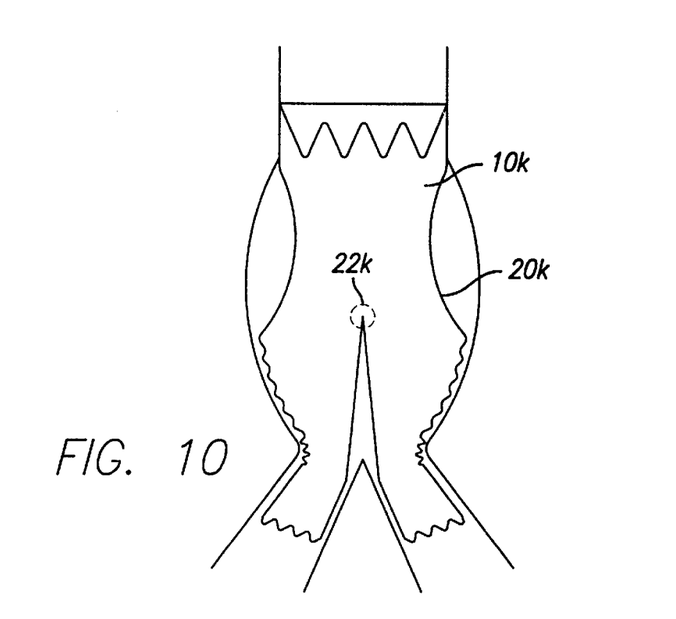
FIG. 10 is a schematic illustration of a vascular graft implanted in an abdominal aortic aneurysm.

Finally, the flare 20j shown in FIG. 6C is in a position inferior to that of the bifurcation point 22j. This configuration can be particularly desirable for avoiding bunching of graft material within the vasculature. For example, FIG. 10 illustrates a graft 10k having a flare 20k located at or superiorly of the bifurcation point 22k (such as the graft of FIG. 6A or 6B). The graft 10k is positioned in an aneurysm of the abdominal aortic artery, with the limbs 14k, 16k positioned in the iliac arteries. If, for example, the graft has a 30 mm diameter trunk and 18 mm diameter limbs, the positioning of the flare 20k will place 36 mm of graft at the patient's native bifurcation (i.e. the point where the iliac arteries branch from the abdominal aortic artery). Positioning the flare at the inferior ends of the limbs 14j, 16j, such as is shown in FIG. 6C, places the flare in a region of the vasculature that is inferior of the native bifurcation and thus minimize the bunching of redundant graft material illustrated in FIG. 10.

Figure 7:
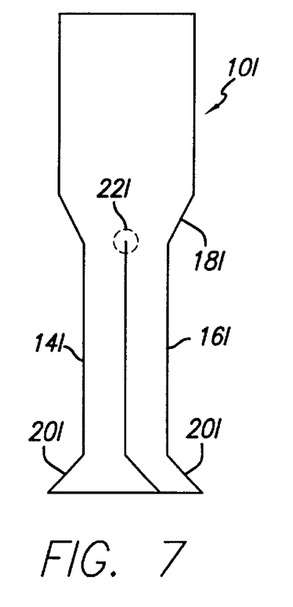
FIG. 7 is a front elevation view of a flared and tapered vascular graft utilizing principles of the present invention.

FIG. 7 shows a further embodiment of a graft 101 which utilizes inferiorly positioned flares 201 of the type shown in FIG. 6C in combination with a taper 181 at a more superior location on the graft.

Figure 8:
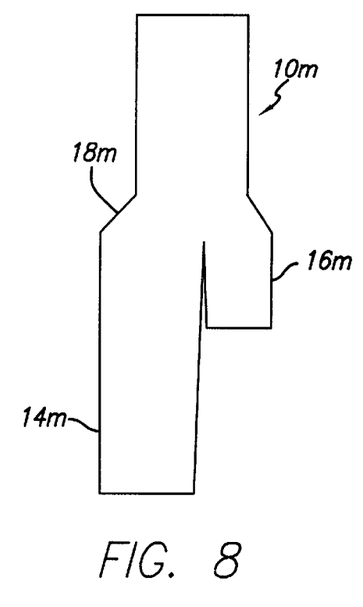
FIG. 8 is a front elevation view of a modular flared vascular graft utilizing principles of the present invention.
Figure 9:
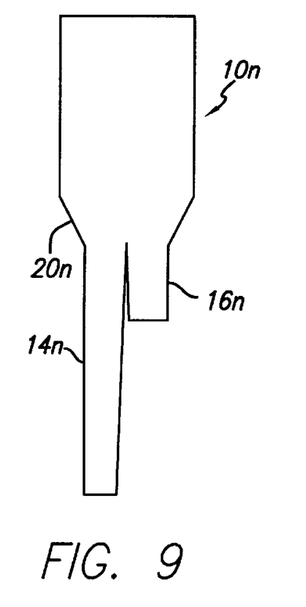
FIG. 9 is a front elevation view of a modular tapered vascular graft utilizing principles of the present invention.

FIGS. 8 and 9 show additional embodiments in which the tapered or flared vascular graft may be provided in modular form, where a "modular graft" is defined as one in which either one or both limbs are not long enough to reach the iliac arteries until a tubular limb extension is added in situ. Limbs may be equal or unequal in length. In contrast, a "unibody graft" is one in which the limbs may be equal or unequal in length, but in which each limb is sufficiently long to reach the iliac arteries.

In the FIG. 8 embodiment, a modular graft having a flare 18m is shown. Naturally, the various features described above (e.g. equal or unequal limb diameters, flare placement, attachment system, equal or unequal limb length etc.) may be utilized in combination with the embodiment of FIG. 8.

In the FIG. 9 embodiment, a modular graft 10n having a taper 20n is shown. Again, the various features discussed above may be utilized for the embodiment of FIG. 9.

Although the invention has been described in connection with specific preferred embodiments, various modifications and variations of the described methods and compositions of the invention will be apparent to those skilled in the art without departing from the scope and spirit of the invention.

We claim:

1. A unibody bifurcated vascular graft comprising:
   a tubular trunk having a diameter;
   a first tubular limb extending from the trunk and having a first limb diameter that is larger or smaller than one-half the trunk diameter; and
   a second tubular limb extending from the trunk and having a second limb diameter;
   wherein the sum of the first and second limb diameters is larger than the trunk diameter.

2. The unibody bifurcated vascular graft of claim 1 wherein the first limb diameter is larger than one-half the trunk diameter.

3. The unibody bifurcated vascular graft of claim 2 wherein the sum of the first and second limb diameters is approximately equivalent to the trunk diameter.

4. The unibody bifurcated vascular graft of claim 2 wherein the first and second limb diameters are approximately equivalent to one another.

5. The unibody vascular graft of claim 2 wherein one of the first or second limb diameters is larger than the other of the first or second limb diameters.

6. The unibody bifurcated vascular graft of claim 1, wherein the first limb diameter is smaller than one-half the trunk diameter.

7. The unibody bifurcated vascular graft of claim 6 wherein the sum of the first and second limb diameters is approximately equivalent to the trunk diameter.

8. The unibody bifurcated vascular graft of claim 6 wherein the first and second limb diameters are approximately equivalent to one another.

9. The unibody bifurcated vascular graft of claim 6 wherein one of the first or second limb diameters is smaller than the other of the first or second limb diameters.

10. The unibody bifurcated vascular graft of claim 1 further including a flared section between the trunk and the first and second limbs.

11. The unibody bifurcated vascular graft of claim 10 wherein the vascular graft is formed of a textile woven from longitudinally extending end yarns and laterally extending pick yarns, and wherein the density of the end yarns is lower in the first limb than it is in the trunk.

12. The unibody bifurcated vascular graft of claim 11 wherein the density of the pick yarns is greater in the first limb than it is in the trunk.

13. The unibody bifurcated vascular graft of claim 1, her including a flared section between the trunk and the first limb.

14. The unibody bifurcated vascular graft of claim 13 wherein the vascular graft is formed of a textile woven from longitudinally extending end yarns and laterally extending pick yarns, and wherein the density of the end yarns is lower in the first limb than it is in the trunk.

15. The unibody bifurcated vascular graft of claim 14 wherein the density of the pick yarns is greater in the first limb than it is in the trunk.

16. The unibody bifurcated vascular graft of claim 1 wherein the tubular trunk includes a superior end and wherein the graft further includes a superior attachment system positioned proximate the superior end.

17. The unibody bifurcated vascular graft of claim 1 wherein the first tubular limb includes an inferior end and wherein the graft further includes an inferior attachment system positioned proximate the inferior end of the first tubular limb.

18. The unibody bifurcated vascular graft of claim 17 wherein the second tubular limb includes an inferior end and wherein the graft further includes an inferior attachment system positioned proximate the inferior end of the second tubular limb.

19. The unibody bifurcated vascular graft of claim 1, wherein the graft includes a bifurcation point between the first and second tubular limbs; and a flare having first and second ends, the first and second ends having a longitudinal position that is superior to the longitudinal position of the bifurcation point.

20. The unibody bifurcated vascular graft of claim 19 wherein the first and second limb diameters are unequal to one another.

21. The unibody bifurcated vascular graft of claim 19, wherein the first and second limbs are unequal in length.

22. The unibody bifurcated vascular graft of claim 21 wherein the first and second limb diameters are unequal to one another.

23. The unibody bifurcated vascular graft of claim 1, wherein the graft includes a bifurcation point between the first and second tubular limbs; and a flare having first and second ends, the first and second ends having a longitudinal position that is inferior of the longitudinal position of the bifurcation point.

24. The unibody bifurcated vascular graft of claim 23 wherein the first and second limb diameters are unequal to one another.

25. The unibody bifurcated vascular graft of claim 23, wherein the first and second limbs are unequal in length.

26. The unibody bifurcated vascular graft of claim 25 wherein the first and second limb diameters are unequal to one another.

27. The unibody bifurcated vascular graft of claim 1, wherein the graft includes a bifurcation point between the first and second tubular limbs; and a flare having first and second ends, the first end having a longitudinal position that is superior to the longitudinal position of the bifurcation point and the second end having a longitudinal position that is inferior of the longitudinal position of the bifurcated point.

28. The unibody bifurcated vascular graft of claim 27 wherein the first and second limb diameters are unequal to one another.

29. The unibody bifurcated vascular graft of claim 27, wherein the first and second limbs are unequal in length.

30. The unibody bifurcated vascular graft of claim 29 wherein the first and second limb diameters are unequal to one another.

31. A method of endovascularly implanting a unibody vascular graft into vessels of a patient, comprising the steps of:

provating a selection of unibody bifurcated vascular grafts each having:

a tubular trunk having a selected diameter;

a first tubular limb extending from the trunk and having a first limb diameter that is larger or smaller than one-half the trunk diameter; and a second tubular limb extending from the trunk and having a second limb diameter;

in which, in the selected vascular graft, the sum of the first and second limb diameters is greater than the trunk diameter;

measuring the vessels of the patient requiring implantation; and endovascularly implanting a selected vascular graft into the patient's vessel.

32. The method of claim 31 in which the selected vascular graft has first and second limb diameters that are unequal to one other.

33. The method of claim 31 in which in the selected vascular graft the sum of the first and second limb diameters is approximately equivalent to the trunk diameter and the first and second limb diameters are unequal to one another.

* * * * *

UNITED STATES PATENT AND TRADEMARK OFFICE
CERTIFICATE OF CORRECTION

PATENT NO.   : 6,454,796 B1
DATED        : September 24, 2002
INVENTOR(S)  : Kimberly Barkman et al.

It is certified that error appears in the above-identified patent and that said Letters Patent is hereby corrected as shown below:

<u>Title page,</u>
Item [56], U.S. PATENT DOCUMENTS, add the following:
-- 5,755,073    5/1998    Evans et al.,
   5,769,885    6/1998    Quiachon et al.,
   5,800,514    9/1998    Nunez et al. --.
Add -- FOREIGN PATENT DOCUMENTS --, followed by:
-- 3-45743      2/1999    [JP],
US98/01066      7/1998    PCT --.

<u>Column 10,</u>
Line 65, change "her", to read -- further --.

Signed and Sealed this

Eleventh Day of February, 2003

JAMES E. ROGAN
*Director of the United States Patent and Trademark Office*